United States Patent [19]
Christopher

[11] Patent Number: 5,515,844
[45] Date of Patent: *May 14, 1996

[54] METHOD AND APPARATUS FOR WEANING VENTILATOR-DEPENDENT PATIENTS

[76] Inventor: Kent L. Christopher, 9086 E. Colorado Cir., Denver, Colo. 80231

[*] Notice: The term of this patent shall not extend beyond the expiration date of Pat. No. 5,419,314.

[21] Appl. No.: 451,513

[22] Filed: May 26, 1995

Related U.S. Application Data

[63] Continuation-in-part of Ser. No. 166,458, Dec. 13, 1993, Pat. No. 5,419,314, which is a continuation-in-part of Ser. No. 863,403, Apr. 3, 1992, Pat. No. 5,279,288, which is a continuation of Ser. No. 431,026, Nov. 2, 1989, Pat. No. 5,101,820.

[51] Int. Cl.$^6$ .................................................. A61M 16/00
[52] U.S. Cl. ........................ 128/200.26; 128/207.14; 128/207.15; 128/207.17; 128/207.29
[58] Field of Search .................... 128/200.26, 207.14, 128/207.15, 207.17, 207.29, DIG. 26

[56] References Cited

U.S. PATENT DOCUMENTS

| | | | |
|---|---|---|---|
| 4,246,897 | 1/1981 | Muto | 128/207.15 |
| 4,852,565 | 8/1989 | Eisele | 128/207.14 |
| 5,026,352 | 6/1991 | Anderson | 128/207.17 |
| 5,188,100 | 2/1993 | Miles et al. | 128/207.17 |
| 5,217,005 | 6/1993 | Weinstein | 128/200.26 |
| 5,217,008 | 6/1993 | Lindholm | 128/200.26 |
| 5,251,616 | 10/1993 | Desch | 128/DIG. 26 |
| 5,419,314 | 5/1995 | Christopher | 128/207.14 |

OTHER PUBLICATIONS

Bivona Medical Technologies product catalog (Apr. 1994).
Tracheal Gas Insufflation during Pressure–control Ventilation, A Nahum et al., American Review of Respiratory Diseases (vol. 146, pp. 1411–1418, 1992).

*Primary Examiner*—Aaron J. Lewis
*Attorney, Agent, or Firm*—Dorr, Carson, Sloan & Birney

[57] ABSTRACT

A method and apparatus for weaning a ventilator-dependent patient employs a transtracheal catheter that is inserted through the patient's tracheostomy tube to continuously augment the flow of oxygen to the lungs as the patient breathes spontaneously. The weaning process involves disconnecting the ventilator from the tracheostomy tube; deflating the tracheostomy tube cuff so that the patient can breathe spontaneously through the upper airway; removably inserting a transtracheal catheter through the tracheostomy tube; and supplying a continuous flow of an oxygen/air mixture through the transtracheal catheter and into the lungs of the patient. The transtracheal catheter is equipped with a button or plug having clips to engage and cover the proximal opening of the tracheostomy tube. In one embodiment, a flexible tracheostomy tube with an adjustable neck flange is used to allow the distal end of the tracheostomy tube to be positioned immediately above the patient's carina. The relative lengths of the tracheostomy tube and the transtracheal catheter are fixed so that the distal end of the transtracheal catheter remains within the tracheostomy tube approximately 1–2 cm from its distal end.

19 Claims, 7 Drawing Sheets

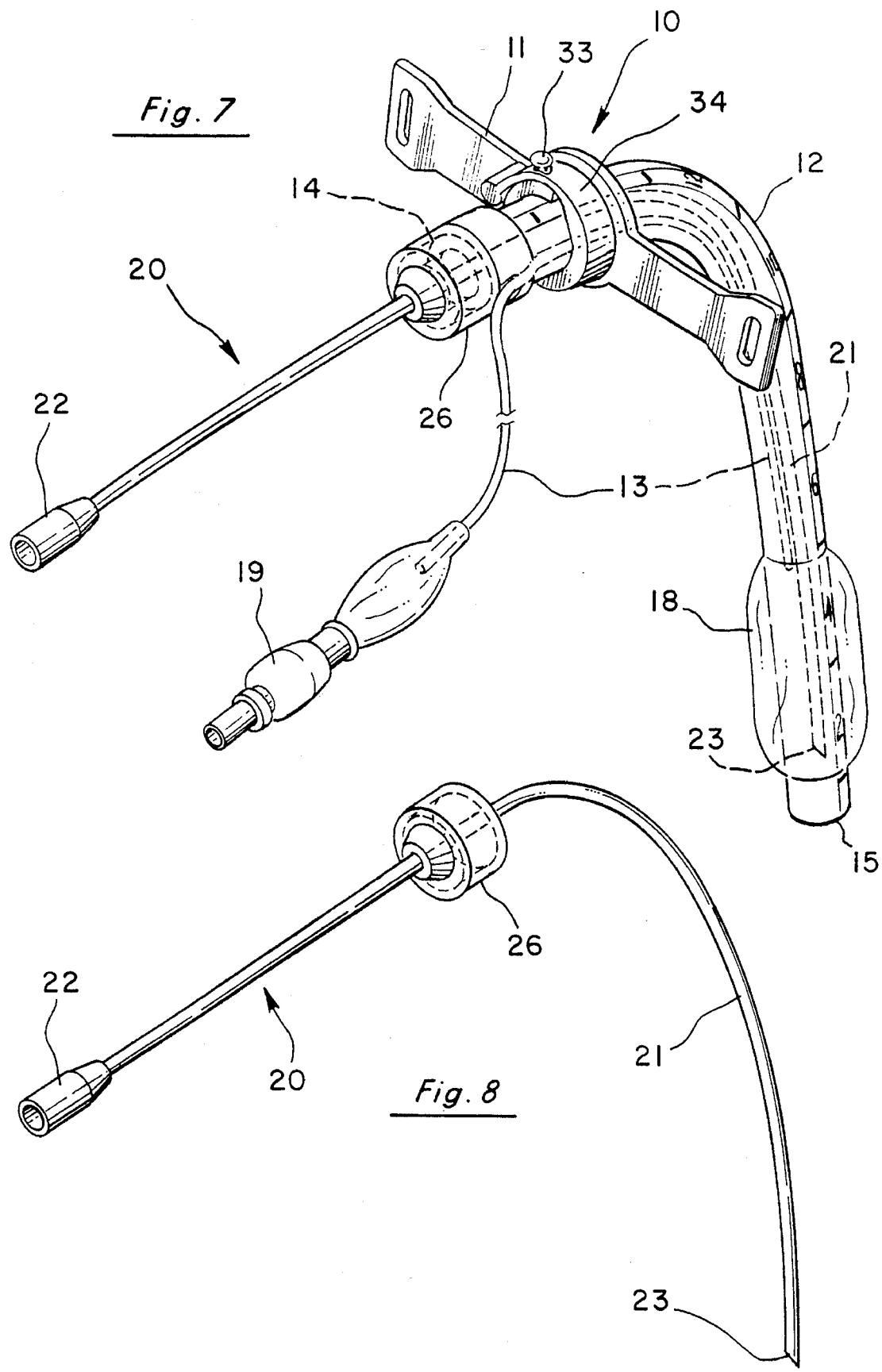

METHOD AND APPARATUS FOR WEANING VENTILATOR-DEPENDENT PATIENTS

RELATED APPLICATION

The present application is a continuation in part of the Applicant's U.S. patent application Ser. No. 08/166,458, entitled "Method and Apparatus for Weaning Ventilator-Dependent Patients" filed on Dec. 13, 1993, now U.S. Pat. No. 5,419,314, which is a continuation in part of the U.S. patent application Ser. No. 07/863,403 entitled "Apparatus for High Continuous Flow Augmentation of Ventilation and Method Therefor" filed on Apr. 3, 1992, now U.S. Pat. No. 5,279,288, which is a continuation of U.S. patent application Ser. No. 07/431,026, filed on Nov. 2, 1989, now U.S. Pat. No. 5,101,820.

BACKGROUND OF THE INVENTION

1. Field of the Invention

The present invention relates generally to the field of systems for weaning a patient from a mechanical ventilator. More specifically, the present invention discloses a method and apparatus for augmenting the flow of oxygen into the patient's lungs during the weaning process by inserting a transtracheal catheter through the tracheostomy tube.

2. Statement of the Problem

Patients with acute lung injury or respiratory failure are often treated by use of a mechanical respirator or ventilator. One of the most common mechanical respiratory units employs a tracheostomy tube inserted into the patient's trachea to force oxygen under pressure into the lungs. The distal portion of the tracheostomy tube includes an inflatable, occluding balloon which functions as a cuff in the throat to minimize retrograde air leaks during the inflation cycle of the ventilator. The ventilator periodically increases and decreases the pressure within the patient's airway to deliver oxygen to, and remove carbon dioxide from the lungs. Virtually the entire flow occurs through the tracheostomy tube.

It is also well known that mechanical ventilation techniques produce detrimental side effects. In particular, the elevated airway pressures during mechanical ventilation can further damage the patient's lungs and greatly increase the risk of barotrauma (for example, subcutaneous emphysema, pneumothorax, and pneumopericardium) and pulmonary interstitial and alveolar edema. Efforts to limit the airway pressure during mechanical ventilation can sometimes result in inadequate blood gas levels. Pressure limits can also result in permissive hypercapnia, in which carbon dioxide levels are allowed to increase. This can cause the pH of the patient's blood to become dangerously acidotic. The patient tends to stay in respiratory failure and the patient's renal, hepatic and cerebral functions can also be impaired.

In addition to damaging the patient's respiratory tree, mechanical ventilation also tends to negate the natural augmentation of venous return that normally attends spontaneous respiration, and decreases cardiovascular output. These factors often create a progressive, downward spiral for patients that have been placed on mechanical ventilation.

As a result of these detrimental side effects, health care professionals attempt to limit the duration of mechanical ventilation to a minimum and to wean patients from mechanical ventilation as soon as possible. The conventional approach for weaning ventilator patients involves periodically removing the patient from the ventilator for increasingly long periods of unassisted breathing. However, an abrupt transition from mechanical ventilation to unassisted breathing is sometimes too difficult for the patient and can result in episodes of acute respiratory distress.

PRIOR ART—TRACHEOSTOMY TUBES

A number of tracheostomy tubes have been invented in the past, including the following:

| Inventor | U.S. Pat. No. | Issue Date |
|---|---|---|
| Eisele | 4,852,565 | Aug. 1, 1989 |
| Muto | 4,246,897 | Jan. 27, 1981 |

Bivona Medical Technologies product catalog (April 1994)

Eisele discloses a fenestrated tracheostomy tube. This tracheostomy tube is widely marketed by Shiley Inc. of Irvine, Calif. The neck flange 24 and outer cannula 30 are made of rigid plastic. The neck flange 24 is secured to the outer cannula 30 by two horizontal pins that permit the neck flange to pivot or swivel through a limited range of motion. However, the pins do not permit the neck flange 24 to slide along the outer cannula 30.

Muto discloses a tracheostomy tube combined with a removable obdurator. The neck flange appears to be fixed relative to the tracheostomy tube.

The product catalog from Bivona Medical Technologies of Gary, Ind., shows a wide variety of conventional tracheostomy tubes. Bivona Medical Technologies markets a line of flexible silicone tracheostomy tubes having adjustable neck flanges, as shown on page 9 of the catalog. The tracheostromy tube is reinforced with an internal helical wire.

PRIOR ART—OPEN DELIVERY SYSTEMS

In contrast to the "closed" ventilators discussed above, a number of open oxygen delivery systems have been invented in the past. Open systems deliver oxygen into the nostril, mouth, or the trachea while keeping the patient's lungs open to the atmosphere. The patient is allowed to continue breathing spontaneously in such open systems. These systems are much more comfortable to the patient than closed systems. For example, the patient is usually permitted to speak, eat, and drink freely. Open delivery systems are typically designed for long-term use by patients who are capable of self-breathing.

One example of an open delivery system is the "SCOOP" transtracheal catheter manufactured by Transtracheal Systems, Inc. of Englewood, Colo., and described in U.S. Pat. Nos. 5,090,408 and 5,181,509. One system for continuous flow augmentation and ventilation of a patient using a transtracheal catheter is discussed in the applicant's U.S. Pat. No. 5,101,820, issued on Apr. 7, 1992. The "SCOOP" transtracheal catheter is made of a bio-polymer of 70–90 Shore A durometer hardness that resists kinking and crushing. The internal tubing is radio-opaque. The total length is approximately 20 to 22 cm. The internal length (from the neck flange to the distal end of the catheter) is approximately 9 cm to 13 cm. The inside diameter of the tubing is 1.7 to 3.0 mm and the outside diameter is 3.5 mm or less. Oxygen flow rates of up to six liters per minute are possible without exceeding the two psi maximum back pressure of conventional delivery systems.

Nahum et al. have suggested combining a conventional closed mechanical ventilation system with tracheal gas insufflation ("TGI") to augment alveolar ventilation without distention or other forms of alveolar damage. Nahum et al., "Tracheal Gas Insufflation During Pressure-Control Ventilation", American Review of Respiratory Diseases (vol. 146, pages 1411–1418, 1992). Constant-flow ventilation (CFV) catheters are positioned in the main bronchi or in the trachea to augment air flow to the patient's lungs without substantially increasing the airway pressure. However, Nahum et al. propose use of TGI in combination with, or as an adjunct to conventional mechanical ventilation systems, and not a means for weaning the patient from mechanical ventilation.

3. Solution to the Problem

None of the prior art references uncovered in the search show a method and apparatus for weaning a patient from a mechanical ventilator by deflating the cuff on the patient's transtracheal catheter and temporarily inserting a transtracheal catheter through the tracheostomy tube to deliver a flow of oxygen into the lungs as the patient breathes spontaneously. The flow rate can be gradually reduced over time. In addition, if the patient encounters respiratory distress during the weaning process, the tracheostomy tube remains in place and can quickly be reconnected to the mechanical ventilator unit. The transtracheal tube can also be easily removed from the tracheostomy tube to allow the patient's secretions to be removed by suction for time to time. One embodiment of the present invention uses a flexible tracheostomy tube with an adjustable neck flange. The position of the neck flange to be adjusted so that the distal end of the tracheostomy tube is located immediately above the patient's carina. This optimizes the effectiveness of transtracheal catheter in inducing the flow of air/oxygen into the lungs and in flushing carbon dioxide from the lungs. The relative lengths of the tracheostomy tube and the transtracheal catheter are also fixed so that following insertion, the distal end of the transtracheal catheter remains approximately 1 to 2 cm above the distal end of the tracheostomy tube. This helps to reduce the risk of mucous balls blocking the distal end of the transtracheal catheter and also creates a more even, diffuse flow of air/oxygen into the trachea and lungs which reduces areas of localized dryness.

SUMMARY OF THE INVENTION

This invention provides a method and apparatus for weaning ventilator-dependent patients employing a transtracheal catheter that is inserted through the patient's tracheostomy tube to continuously augment the flow of oxygen to the lungs as the patient breathes spontaneously. The weaning process involves disconnecting the ventilator from the tracheostomy tube; deflating the tracheostomy tube cuff so that the patient can breathe spontaneously through the upper airway; removably inserting a transtracheal catheter through the tracheostomy tube; and supplying a continuous flow of an oxygen/air mixture through the transtracheal catheter and into the lungs of the patient. The transtracheal catheter is equipped with a button or plug having clips to engage and cover the proximal opening of the tracheostomy tube. In one embodiment, a flexible tracheostomy tube with an adjustable neck flange is used to allow the distal end of the tracheostomy tube to be positioned immediately above the patient's carina. The relative lengths of the tracheostomy tube and the transtracheal catheter are fixed so that the distal end of the transtracheal catheter remains within the tracheostomy tube approximately 1–2 cm from its distal end.

A primary object of the present invention is to provide a method and apparatus for safely and effectively weaning ventilator-dependent patients that could not be readily weaned using conventional approaches.

Another object of the present invention is to provide a method and apparatus for reducing the time necessary to wean a patient from mechanical ventilation.

Yet another object of the present invention is to provide a method and apparatus for weaning ventilator-dependent patients that allows the patient to speak and regain use of the glottis as a variable regulator of expiratory air flow.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 7 is a front perspective view of a flexible tracheostomy tube and transtracheal catheter in an alternative embodiment of the present invention.

FIG. 8 is a front perspective view of an alternative embodiment of the transtracheal catheter for use in association with the flexible tracheostomy tube.

DETAILED DESCRIPTION OF THE INVENTION

Figure 1:
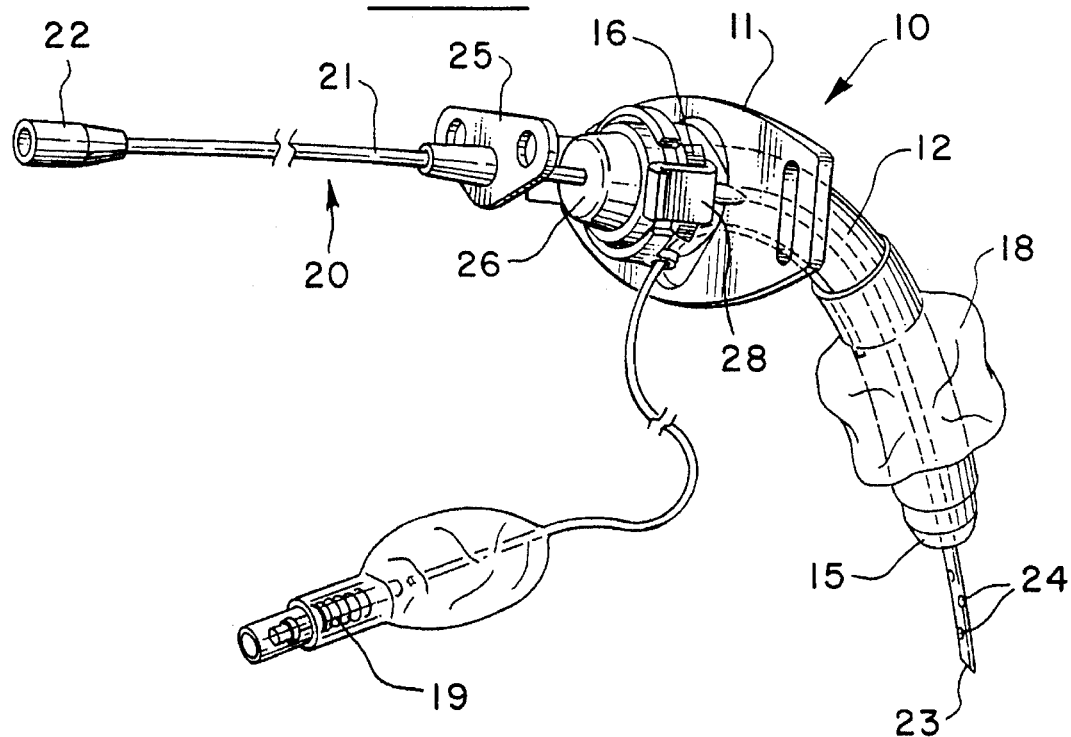
FIG. 1 is a front perspective view of the modified tracheostomy tube and transtracheal catheter.

Turning to FIG. 1, a perspective view is provided of the tracheostomy tube 10 as modified to receive a transtracheal catheter 20. The tracheostomy tube 10 is shown in greater detail in the rear perspective view illustrated in FIG. 3. The tracheostomy tube includes an elongated tube 12 having a generally conventional configuration and dimensions. The inside diameter of the tracheostomy tube must be sufficiently large to accommodate the transtracheal catheter, as will be described below. For example, an inside diameter of approximately 5 millimeters is sufficient.

The distal end 15 of the tracheostomy tube is normally inserted through an incision through the patient's neck 40 and into the trachea 42 before the patient is first attached to the ventilator. A flange 11 extends outward from the tracheostomy tube at a predetermined location so that the flange abuts the patient's neck when the tracheostomy tube is properly inserted. An inflatable cuff 18 located around the distal end 15 of the tracheostomy tube is then inflated by directing air through the valve 19 shown in FIG. 1. After inflation is completed, the cuff 18 substantially seals the region between the distal end of the tracheostomy tube and patient's trachea. This is necessary to allow the ventilator to pressurize the patient's lungs to simulate inhalation, rather than allowing gas to immediately escape through the patient's upper airway. However, as a byproduct, the patient is no longer able to speak because there is no longer air flow through the larynx.

A removable inner cannula 13 can be inserted through the proximal opening 14 of the tracheostomy tube and locked in place. The patient is then connected to the ventilator by attaching the supply tube from the ventilator to a connector at the proximal end of the cannula 13.

Figure 3:
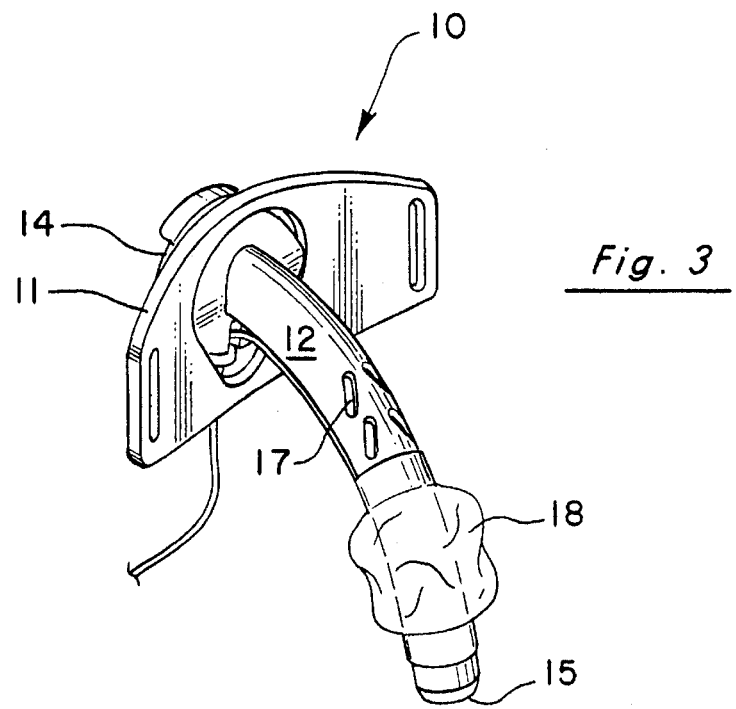
FIG. 3 is a rear perspective view of the modified tracheostomy tube.

The tracheostomy tube has been modified in the preferred embodiment to incorporate two additional elements. First, a number of outwardly extending ears 16 have been added adjacent to the proximal opening 14 of the tracheostomy tube, as shown in FIG. 1. These ears 16 are used to engage corresponding clips 28 on the transtracheal catheter, as will be discussed below. Second, a number of small fenestrations 17 have been added through the distal portion of the tracheostomy tube as shown in FIG. 3. These fenestrations 17 reduce resistance to air flow through the patient's upper airway after the cuff 18 has been deflated and the patient resumes spontaneous breathing as part of the weaning process described below.

Figure 2:
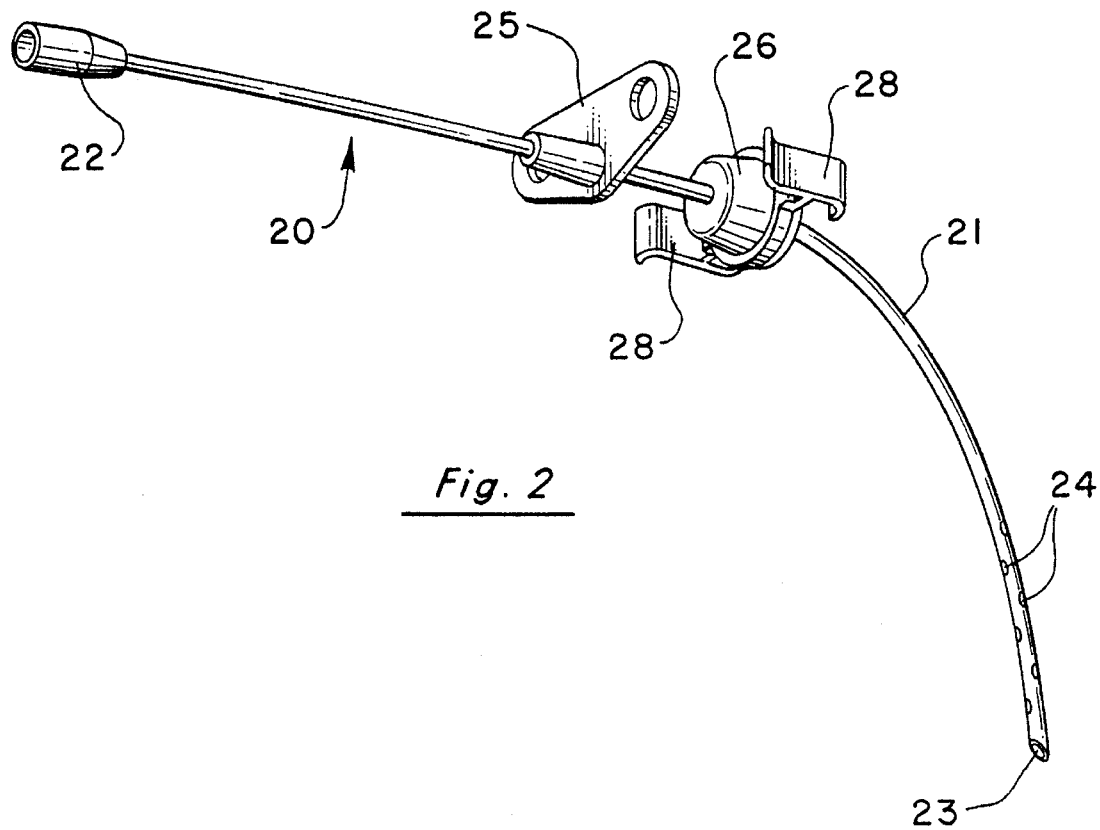
FIG. 2 is a front perspective view of the modified transtracheal catheter.

A more detailed perspective view of the transtracheal catheter 20 is provided in FIG. 2. The transtracheal catheter 20 generally consists of an elongated flexible tube 21 having an outside diameter of approximately 3.5 mm or less and an inside diameter of approximately 1.7 to 3 mm. The total length is approximately 20 to 22 cm and the internal length from the flange 25 to the distal end 23 of the catheter is in the range of approximately 9 to 13 cm. A connector 22 is employed to connect an air/oxygen supply to the proximal end of the tube. In the preferred embodiment the air/oxygen supply provides a flow of gas having an oxygen content of at least 21%. In addition the temperature and relative humidity of the air/oxygen supply can be regulated by including a heater and humidifier. The transtracheal catheter has an opening at its distal end 23 and a number of optional openings 24 in the side wall of the distal portion of the tube 21 to facilitate the flow of gas down the patient's trachea and into the lungs.

Figure 6:
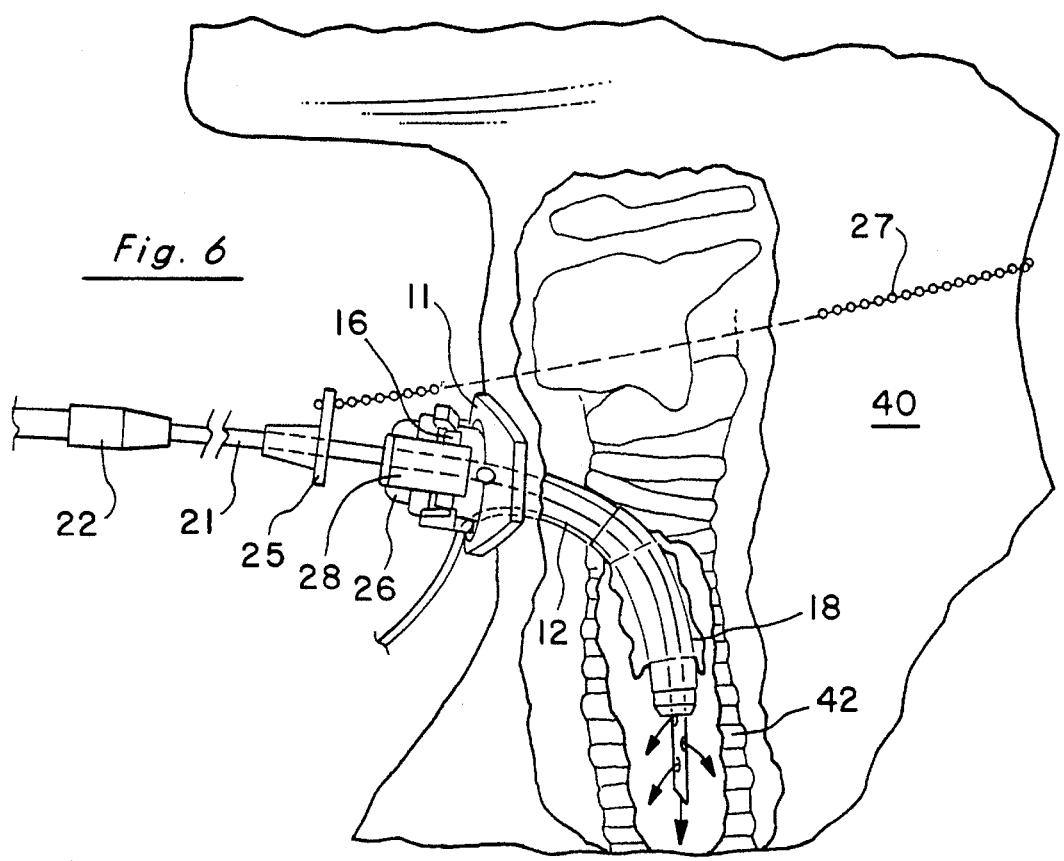
FIG. 6 is a cross-sectional view of the modified tracheostomy tube corresponding to FIG. 4, after the transtracheal catheter has been inserted through the tracheostomy tube.

A button 26 extends radially outward from the tube 21 to at least partially block the proximal opening 14 of the tracheostomy tube 10 when the transtracheal catheter is inserted into the tracheostomy tube, as shown in FIGS. 1 and 6. A number of flexible clips 28 engage corresponding ears 16 located adjacent to the proximal opening 14 of the tracheostomy tube to removably secure the transtracheal catheter 20 (and the button 26) relative to the proximal opening 14 of the tracheostomy tube. In addition, a flange 25 extends from the proximal portion of the tube 21 and can be used in conjunction with a small chain 27 to hold the assembly in place as shown in FIG. 6.

Figure 4:
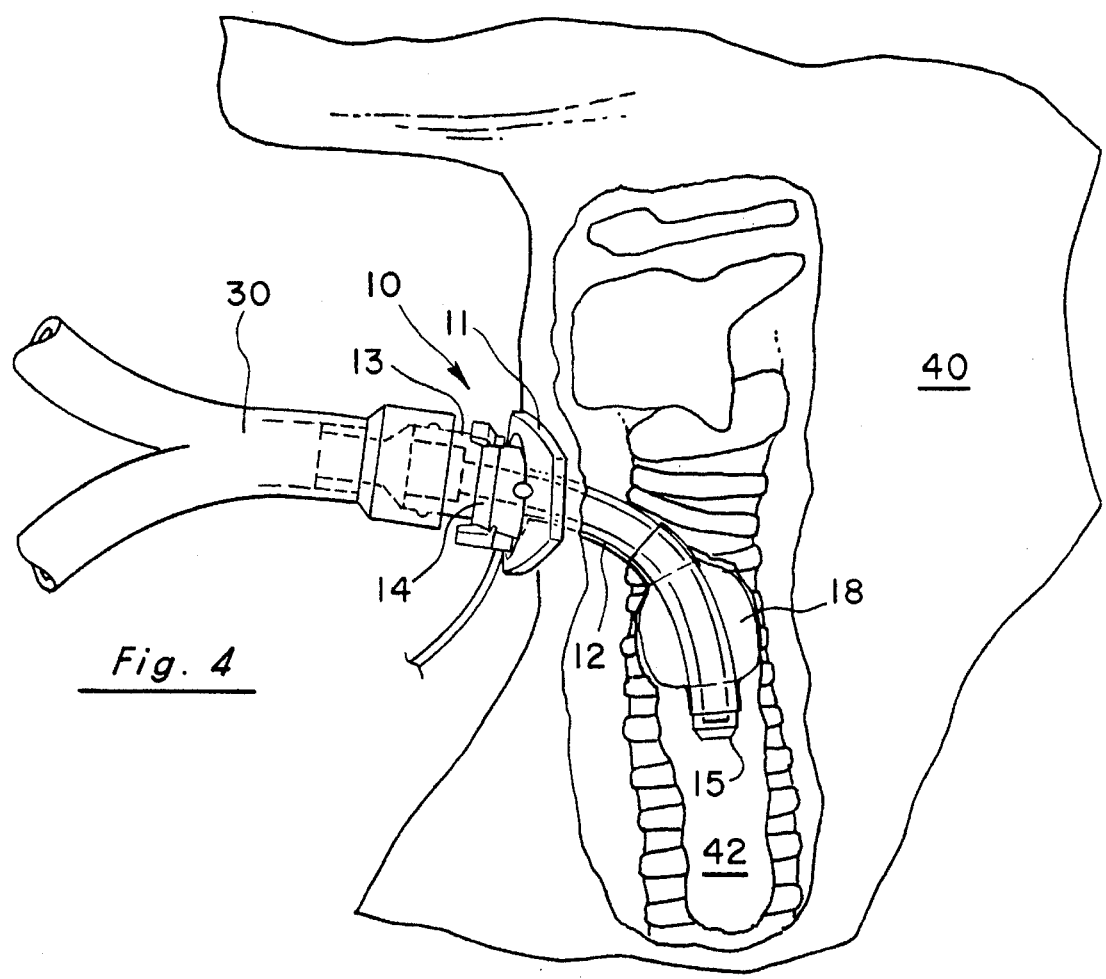
FIG. 4 is a cross-sectional view of the modified tracheostomy tube inserted into the trachea while the patient is attached to a ventilator.
Figure 5:
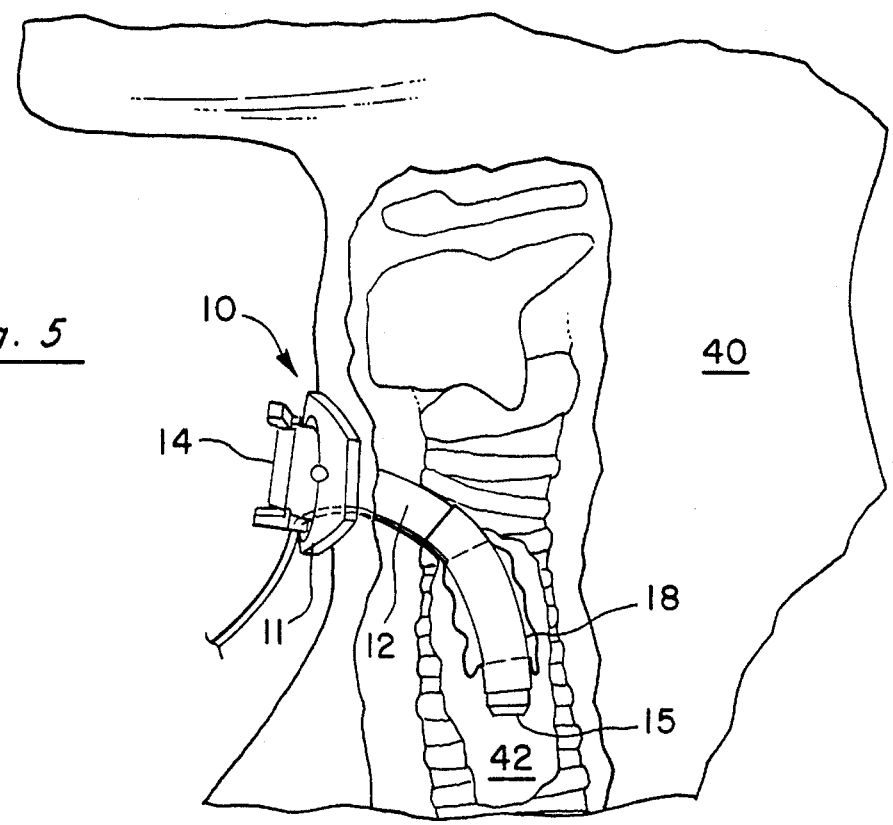
FIG. 5 is a cross-sectional view of the modified tracheostomy tube corresponding to FIG. 4, after the ventilator has been disconnected from the patient, the cannula has been removed from the tracheostomy tube, and the cuff of the tracheostomy tube has been deflated.

FIGS. 4 through 6 illustrate the steps used in the present invention to wean a ventilator-dependent patient 40. FIG. 4 shows the tubular distal portion 12 of the tracheostomy tube 10 inserted through an incision into the patient's trachea 42 in the conventional manner with the flange 11 abutting the front of the patient's neck. The inflatable cuff 18 adjacent to the distal opening 15 of the tracheostomy tube is inflated to seal the region between the tracheostomy tube and the patient's trachea. This effectively prevents the patient from spontaneously breathing through the patient's upper airway. An inner cannula 13 extends within the tubular portion 12 of the tracheostomy from its proximal opening. A connector at the proximal end of the cannula 13 serves both to removably secure the cannula to the proximal opening 14 of the tracheostomy tube 10 and also to attach the cannula 13 to an external ventilator through a connecting tube 30. In this mode, the ventilator alternately increases and decreases the pressure through the tracheostomy tube in the conventional manner to deliver oxygen to, and remove carbon dioxide from the patient's lungs.

FIG. 5 illustrates the next step in the weaning process. The ventilator is disconnected by removing the connecting tube 30 from the cannula 13. The cannula 13 can then be detached and removed from the tracheostomy tube 10 by rotating its proximal end by approximately 90 degrees. Finally, the cuff 18 is deflated by opening the valve 19 shown in FIG. 1 to allow air to escape from the cuff. This permits the patient to begin to breathe spontaneously around the tracheostomy tube and through the patient's upper airway.

FIG. 6 shows the final steps in the process. A modified transtracheal catheter is inserted through the proximal opening of the tracheostomy tube to a position in which the transtracheal catheter's button 26 substantially blocks the proximal opening of the tracheostomy tube. The transtracheal catheter is then secured in place by a number of clips 28 that engage corresponding ears 16 extending outward around the proximal opening 14 of the tracheostomy tube 16. FIG. 1 is a corresponding perspective view of the transtracheal catheter 10 inserted into the tracheostomy tube 20. The distal tubular portion 21 of the transtracheal catheter passes completely through the tracheostomy tube so that its end 23 and associated openings 24 extend into the trachea 42 to a position above the patient's carina. The proximal end of the transtracheal catheter bears a connector 22 that can be removably attached to an air/oxygen supply. This air/oxygen mixture continuously flows through the transtracheal catheter and into the lungs of the patient. The transtracheal catheter can also be held in place by a small chain 27 that runs around the patient's neck and is removably fastened to a flange 25 extending from the proximal portion of the transtracheal catheter as shown in FIG. 6.

The air/oxygen mixture delivered through the transtracheal catheter augments the flow of oxygen into the lungs and tends to assist in flushing carbon dioxide from the lungs. The patient can now breathe spontaneously using the upper airway. Air flows around the tracheostomy tube and through the fenestrations 17 shown in FIG. 3. This permits the patient to speak, more or less naturally, and also allows the patient to use the glottis to regulate air flow. These features will likely have a significant favorable result on the patient's outlook and physiology.

In the preferred embodiment of the present invention, the initial flow rate of the air/oxygen mixture through the transtracheal catheter is in the range of approximately 8 to 20 liters per minute, and preferably about 10 liters per minute. This flow rate can be readily achieved with a back pressure of approximately 2 to 25 psi typically available from conventional oxygen supply systems. The flow rate can be gradually reduced to a minimal value as the patient's spontaneous breathing capacity increases over time. The oxygen content of the mixture supplied through the transtracheal catheter can also be adjusted. Normally, the mixture contains a minimum of 21 percent oxygen, although a higher oxygen content may be required for certain patients. The air/oxygen mixture is typically delivered at a temperature of approximately 35° to 38° and a relative humidity in the range of approximately 80 to 100 percent to maximize patient comfort and minimize the drying effect of oxygen on the mucous membranes.

Since the tracheostomy tube remains in place throughout weaning, the process can be quickly and easily reversed to reattach the patient to the ventilator if the patient encounters difficulty. The transtracheal tube can also be easily removed from the tracheostomy tube to allow the patient's secretions to be removed by suction for time to time.

The basic weaning process discussed above can be modified to intermittently reconnect the patient to mechanical ventilation. In this modified process, the patient is first disconnected from the ventilator and a transtracheal catheter is inserted through the tracheostomy tube to augment oxygen flow into the patient's lungs as discussed above. The patient remains in this mode for an initial period of time, which may vary depending upon the patient's condition and response to the weaning process. The patient is then reattached to the ventilator for a period of time by removing the transtracheal catheter 20 from the tracheostomy tube 10, reinflating the cuff 18, reinserting the inner cannula 13 through the proximal opening 14 of the tracheostomy tube, and reconnecting the ventilator to the cannula at the proximal opening of the tracheostomy tube. The patient then remains attached to the ventilator for a period of time, again depending on the patient's condition and response to the weaning process. This sequence of steps is iteratively repeated while progressively increasing the length of time that the patient is disconnected from ventilator support during each iteration. In addition, the length of time that the patient is connected to the ventilator can be shortened during each iteration.

CASE STUDIES

Eleven ventilator-dependent patents were selected for study. Each patient had previously failed multiple attempts to be weaned from mechanical ventilation. The median age of the patients was 64 years. Diagnoses included chronic obstructive pulmonary disease (or COPD) (9 patients), post polio syndrome (1 patient), and muscular dystrophy (1 patient). Ten patients were female and one was male. The total number of days on mechanical ventilation was 1,290.

Each patient was initially weaned using pressure support ventilation (PSV) down to a pressure of 6 cm of water using a large diameter tracheostomy tube. In particular, a model 7200 PSV unit manufactured by Puritan-Bennett Corp. (Carlsbad, Calif.) was used in conjunction with a #7 or #8 tracheostomy tube manufactured by Shiley Inc. (Irvine, Calif.). A fiber optic examination of the upper airway was done to rule out glottic or tracheal obstruction, since an upper airway obstruction would constitute a contra-indication for transtracheal augmentation of ventilation. The patients' arterial blood gases were then assessed under the following test conditions:

1. Pressure support ventilation (PSV) using a #7 or #8 tracheostomy tube.
2. Conventional T-piece trial weaning with the same tracheostomy tube.
3. Pressure support ventilation (PSV) with a Shiley #4 fenestrated cuffed tracheostomy tube and a pressure support setting to achieve similar volumes to test condition 1;
4. The present method using a transtracheal catheter to augment ventilation.

During the fourth test condition implementing the present invention, the inner cannula of the tracheostomy tube was removed and the cuff was deflated. A transtracheal catheter (model SCOOP-1, Transtracheal Systems, Inc., Englewood, Colo.) was placed within the lumen of the tracheostomy tube using a button with clips, as previously discussed. An oxygen/air mixture was delivered through the transtracheal catheter at a flow rate of approximately 10 liters per minute via a heated wire circuit from a servo-controlled pass-over humidifier (Bird Medical Products, Palm Springs, Calif.) to regulate the temperature and humidity of the oxygen/air mixture. In contrast to breathing through a tracheostomy tube, patients using transtracheal augmentation breathed via the upper airway (i.e., around the tracheostomy tube and through the fenestrations) thus allowing them to speak and regulate gas flow through the glottis.

Arterial blood gases were obtained under each of the four test conditions. An esophageal balloon was placed to allow for assessment of respiratory mechanics (BICORE, Monitoring Systems, Inc., Irvine, Calif.). Tidal volume (Vt) and respiratory rate (RR) were measured at the tracheostomy tube (in test conditions 1–3) or the mouth (in test condition 4). In test condition 4, the transtracheal flow was integrated over the inspiratory time from the respiratory duty cycle (Ti/Ttot) and added to the mouth volume to reflect the corrected, or true inspired tidal volume ($Vt_{COR}$). The pressure-time product was averaged over ten breaths and multiplied by the respiratory rate (RR) to yield the pressure-time index (PTI). Finally, respiratory drive ($P_{0.1}$) was measured and minute ventilation was calculated as the product of respiratory rate (RR) and tidal volume (Vt for test conditions 1–3, and $Vt_{COR}$ for test condition 4). The arterial blood gas results under each of the test conditions are shown below. All values are expressed as a mean +/– a standard deviation.

| | Arterial Blood Gas Results | | | |
|---|---|---|---|---|
| | $PaO_2$ (mm Hg) | $PaCO_2$ (mm Hg) | pH | $SaO_2$(%) |
| PSV (#7–8) | 82.0 ± 20.4 | 47.5 ± 13 | 7.43 ± .1 | 92.6 ± 3.0 |
| T-Piece | 100 ± 37.6 | 52.5 ± 9.6 | 7.38 ± .1 | 93.9 ± 2.7 |
| PSV (#4) | 88.1 ± 26.1 | 48 ± 10.5 | 7.41 ± .1 | 93.2 ± 3.1 |
| Transtracheal Augmentation | 77.6 ± 11.2 | 51 ± 11.1 | 7.39 ± .1 | 92.9 ± 1.6 |

Although $PaCO_2$ was higher and pH lower with conventional T-piece weaning (test condition 2) compared to PSV with a #7 or #8 tracheostomy tube (test condition 1), the results were clinically equivalent for each of the test conditions. The results of the assessment of respiratory mechanics are shown in the following table. Again, all values are expressed as a mean +/– a standard deviation.

| | Respiratory Mechanics | | | |
|---|---|---|---|---|
| | PSV (#7–8) | PSV (#4) | T-Piece | Transtracheal Augmentation |
| RR (per min) | 24.5 ± 4.6 | 22.5 ± 8.6 | 27.4 ± 6.7 | 24.6 ± 5.0 |
| MV (liters) | 7.8 ± 3.0 | 7.1 ± 2.1 | 5.96 ± 2.1 | 2.40 ± 1.3 |

-continued

| Respiratory Mechanics | | | | |
|---|---|---|---|---|
| | PSV (#7–8) | PSV (#4) | T-Piece | Transtracheal Augmentation |
| $MV_{COR}$ (liters) | — | — | — | $5.69 \pm 1.5$ |
| PTI (cm-sec) | $89 \pm 48$ | $109 \pm 110$ | $183 \pm 56$ | $186 \pm 64$ |
| Ti/Ttot | $0.42 \pm 0.07$ | $0.38 \pm 0.06$ | $0.41 \pm 0.06$ | $0.41 \pm 0.07$ |
| $P_{0.1}$ (cm $H_2O$) | $3.5 \pm 0.7$ | $3.5 \pm 1.9$ | $4.1 \pm 1.5$ | $3.4 \pm 1.3$ |

There were no significant differences among the four test conditions in respiratory drive ($P_{0.1}$) or the respiratory duty cycle (Ti/Ttot). As expected, minute ventilation tended to be higher and oxygen cost of breathing (PTI) lower when comparing both PSV conditions (test conditions 1 and 3) to spontaneous breathing modes (test conditions 2 and 4). Likewise, respiratory rates were lower when comparing both PSV conditions to T-piece weaning (test condition 2), but results were clinically equivalent. With respect to test conditions 2 and 4, there were no significant differences in respiratory rate (RR) or PTI. Although the $MV_{COR}$ with transtracheal catheter augmentation was similar to MV with T-piece weaning, over 60% of the inspired volume came from the transtracheal bias flow and not from the mouth.

All eleven patients preferred transtracheal catheter augmentation to any of the other test conditions. A total of seven patients were successfully weaned from mechanical ventilation and were discharged to their homes using the present invention. The time required to wean off PSV to transtracheal catheter augmentation was a mean of 9.5 days. Patients were weaned off transtracheal augmentation and decannulated by a mean of an additional 3.2 days. In addition to having failed multiple weaning attempts using a variety of weaning techniques, this group of patients had been ventilator dependent for a mean of 68 days prior to beginning transtracheal augmentation weaning trials using the present invention.

Of the remaining four patients, three were able to be weaned for up to 24 hours on transtracheal augmentation. At that point, two patients developed non-pulmonary complications (renal failure and cardiac failure) that necessitated reinstitution of mechanical ventilation and ultimately resulted in their deaths. The third patient had muscular dystrophy with rapidly progressive weakness and it was concluded that long-term nocturnal ventilation was necessary. The fourth patient tolerated up to nine hours per day of transtracheal augmentation, but was found to be psychologically dependent upon the ventilator. She returned home on mechanical ventilation.

Based on the results of this small study, a number of tentative conclusions can be drawn:

A. The present invention is similar to conventional T-piece weaning and the two PSV test conditions with respect to arterial blood gases.
B. The present invention is similar to conventional T-piece weaning with regard to respiratory rate, corrected minute ventilation, respiratory duty cycle, ventilatory drive, and oxygen cost breathing.
C. Using the present invention, approximately 60% of the minute ventilation was delivered via the transtracheal catheter.
D. The present invention is well tolerated and safe.
E. All eleven patients preferred transtracheal augmentation to either conventional T-piece weaning or PSV.
F. Seven of the eleven "difficult to wean" patients were successfully weaned and discharged home using the present invention.

The ability to communicate may have improved the patients' attitude and self image, and this factor may have played a role in successful weaning. In addition, the fact that patients were able to use their glottis to regulate air flow may have resulted in a beneficial physiologic response that was not addressed by the blood gases or the respiratory mechanics evaluated in this study.

Following the physiological studies, the patients were placed on pressure support ventilation using a #4 tracheostomy tube, and were then weaned for progressively longer periods of time using transtracheal catheter augmentation. Once weaned to transtracheal catheter augmentation for periods up to 24 hours, subjects were advanced to standard transtracheal oxygen delivery for a 24-hour period. At that point, the patients were considered weaned and the tracheostomy tube was removed.

ALTERNATIVE EMBODIMENT

Figure 9:
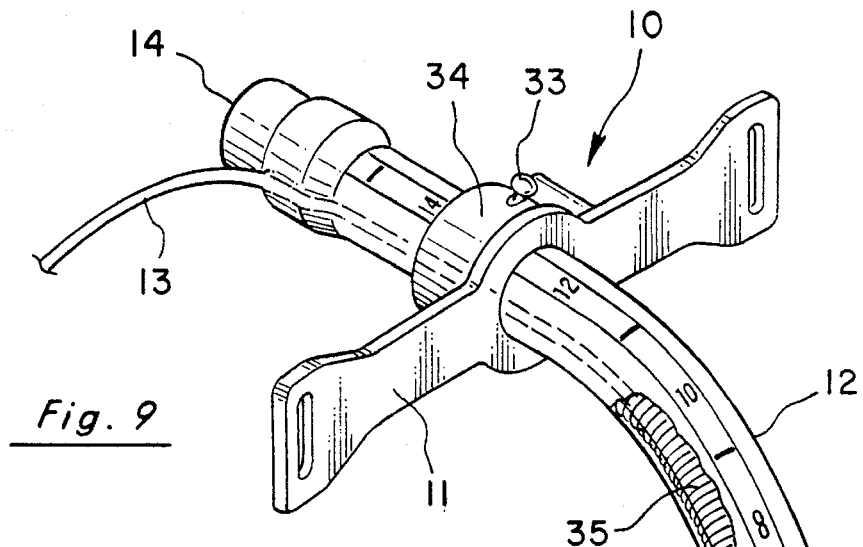
FIG. 9 is a rear perspective view of the flexible tracheostomy tube in the alternative embodiment corresponding to FIG. 7.

FIGS. 7–12 show another embodiment of the present invention using a flexible tracheostomy tube 10 with an adjustable neck flange 11 in place of the previous rigid tracheostomy tube shown in FIGS. 1–6. The tracheostomy tube assembly depicted in FIG. 9 includes a flexible tube 10 with a proximal opening 14 suitable for connection to the ventilator, and a distal portion 12 with an opening 15 for insertion through an incision into the patient's trachea 42. The tracheostomy tube 10 can be made of silicone rubber (or another flexible biocompatible material) and has a length of about 12 or 13 cm and an inside diameter of approximately 4 to 6 mm. A helical reinforcing wire 35 can be embedded in the tube for structural support and to help prevent kinking or crimping of the tube. An inflatable cuff 18 surrounds the distal end of the tracheostomy tube 12, as in the previous embodiment. Inflation of the cuff 18 is controlled by a value 19 connected to the cuff through a small tube 13 that leads from the valve 19 and is bonded to the surface of the tracheostomy tube 10 as shown in FIGS. 7 and 9.

As shown in FIG. 9, an adjustable neck flange 11 slides relative to the tracheostomy tube 10 and can be manually positioned at any desired location along its length. The position of the neck flange 11 along the tracheostomy tube 10 controls the length of the distal portion 12 of the tracheostomy tube 10 inserted into the patient's trachea 42. As shown in FIGS. 7 and 9, a series of radio-opaque markings extend along the length of the tracheostomy tube 10. These markings permit the health care provider to visually check whether the neck flange 11 has moved from its desired position on the tracheostomy tube. The markings also permit the health care provider to clearly observe the position of the distal end 15 of the tracheostomy tube 10 within the patient's trachea by means of x-ray imaging.

The neck flange 11 is typically made of silicone rubber. The resulting high degree of friction between the tracheostomy tube 10 and neck flange 11 is sufficient to hold the neck flange in place relative to the tracheostomy tube unless significant axial force is applied. However, the neck flange 11 can be equipped with a strap 34 that extends around the opening in the flange 11 adjacent to the tracheostomy tube 10. The strap 34 can be removably fastened to a small post 33 extending from the neck flange 11 to constrict the flange opening and thereby prevent the neck flange from sliding relative to the tracheostomy tube 10.

Flexible tracheostomy tubes, such as the devices marketed by Bivona Medical Technologies, were originally developed to accommodate differences in patient anatomy.

Figure 12:
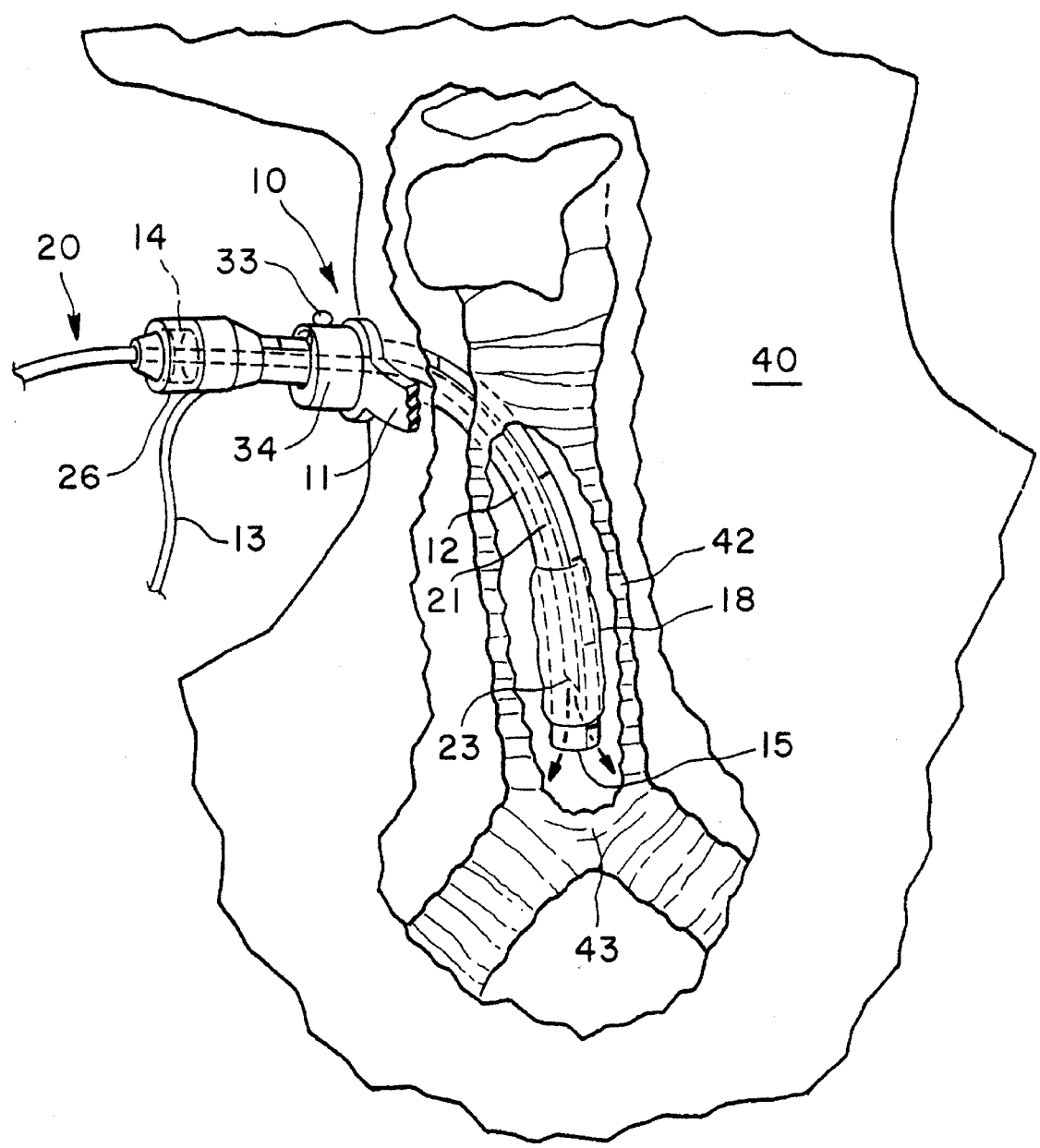
FIG. 12 is a cross-sectional view of the flexible tracheostomy tube corresponding to FIG. 9, after the transtracheal catheter has been inserted through the tracheostomy tube.

However, the present invention is based on a recognition that a flexible tracheostomy tube allows the tracheostomy tube to freely bend as it is inserted and accommodates adjustment in the length of the distal portion of the tracheostomy tube as the position of the neck flange is changed. This permits that health care provider to easily adjust the position of the neck flange so that the distal end 15 of the tracheostomy tube 10 is positioned immediately above the patient's carina 43 as shown in FIG. 12. As previously discussed, this position has been demonstrated as being optimal for increasing oxygenation of the patient's bloodstream and for removing carbon dioxide from the patient's lungs.

The transtracheal catheter 20 shown in FIG. 8 is generally configured as previous described and shown in the first embodiment in FIGS. 1–6. In the preferred embodiment, the transtracheal catheter 20 has a total length of about 20 to 22 cm, an inside diameter of about 1.7 to 3 mm, and an outside diameter of approximately 3.5 mm or less. The distal portion 21 of the transtracheal catheter 20 can be removably inserted through the proximal opening 14 of the tracheostomy tube 10. However, the distal portion 21 of the transtracheal catheter (i.e., distal from the cap 26) is shorter than the length of the tracheostomy tube 10 so that the distal end 23 of the transtracheal catheter 20 remains within the tracheostomy tube 10. In the preferred embodiment, the length of the distal portion 21 of the transtracheal catheter 20 is about 11 cm, which results in the distal end of the transtracheal catheter 23 being located approximately 1 to 2 cm above the distal end 15 of the tracheostomy tube 10. This helps to reduce the risk of mucous balls blocking the distal end of the transtracheal catheter and also creates a more even, diffuse flow into the trachea which reduces irritation of the respiratory mucosa. As in the first embodiment, the transtracheal catheter 20 includes an opening at its distal end 23. A number of optional side ports can also be included in the side wall of the distal portion of the tube 21 to provide a more diffuse flow of gas.

The slidable neck flange 11 also permits the assembly to be designed with a fixed relationship between the length of the tracheostomy tube 10 and the length of the transtracheal catheter 20. Differences in patient size and anatomy are handled simply by adjusting the position of the neck flange 11 while the position of the transtracheal catheter 20 remains fixed relative to the tracheostomy tube 10 after insertion. Thus, the total length of the tracheostomy tube 10 and the length of transtracheal catheter 20 remain constant, regardless of the position of the neck flange 11. This virtually eliminates the need for transtracheal catheters 20 of different lengths, and allows ancilliary equipment (e.g., cleaning rods) to be standardized on a single size.

Figure 10:
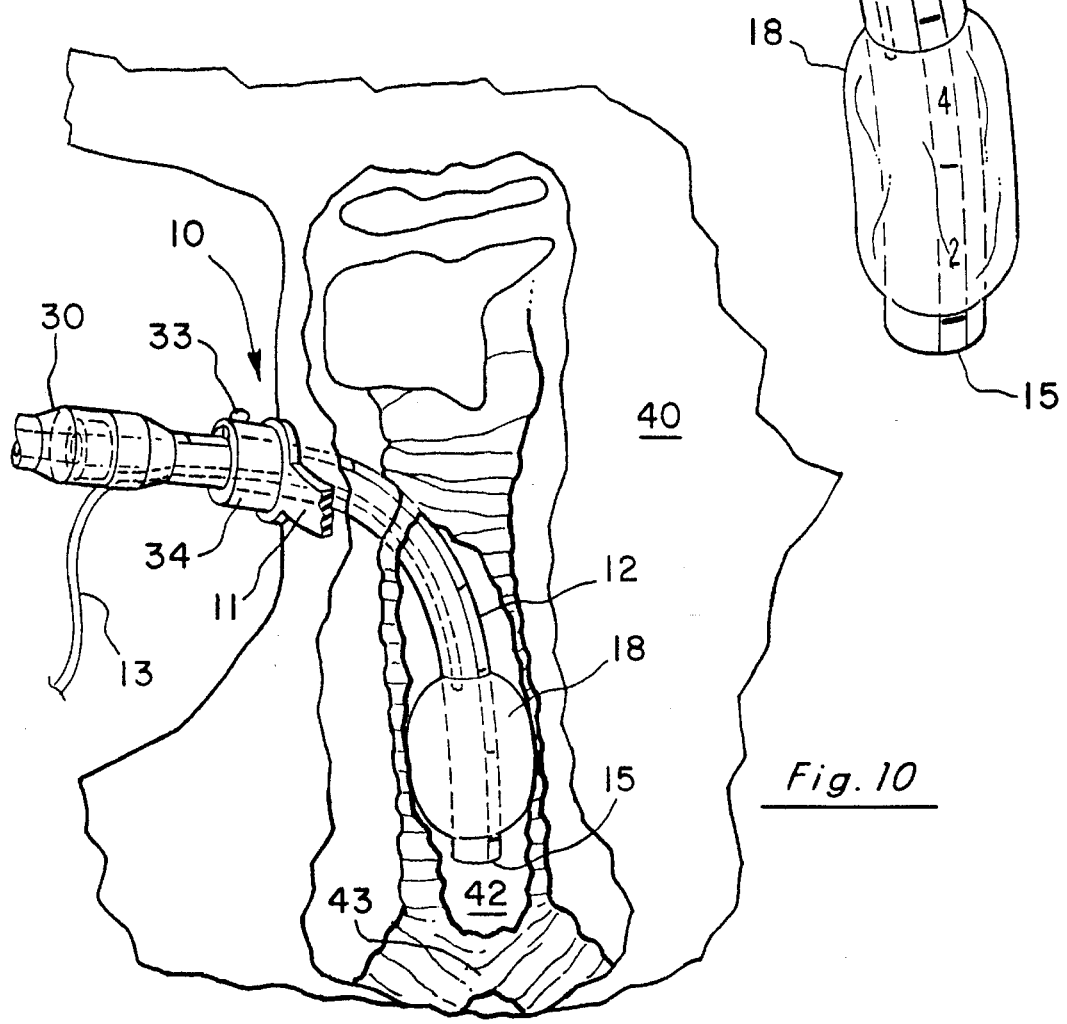
FIG. 10 is a cross-sectional view of the flexible tracheostomy tube inserted into the trachea while the patient is attached to a ventilator in the alternative embodiment.

A cap 26 extends outward from the transtracheal catheter 20 to fit over the proximal opening 14 of the tracheostomy tube 10 when the distal portion 21 of the transtracheal catheter 20 is inserted into the tracheostomy tube 10. This cap 26 can include clips similar to those shown in FIG. 1 for removably securing the transtracheal catheter 20 to the proximal opening 14 of the tracheostomy tube 10. Alternatively, the cap 26 can provide a friction fit around the proximal opening 14 of the tracheostomy tube 10 as illustrated in FIGS. 7 and 12. In this case, the cap 26 is sized to be interchangeable with the standard ventilator cap 30 used to connect a ventilator to the proximal opening 14 of the tracheostomy tube 10 as shown in FIG. 10. In yet another alternative embodiment, the cap 26 could be replaced with a button or tapered plug that is insertable into the proximal opening 14 of the tracheostomy tube 10. A Luer-Lok™ connection could also be employed to fasten the transtracheal catheter 20 into the proximal opening 14 of the tracheostomy tube 10.

Figure 11:
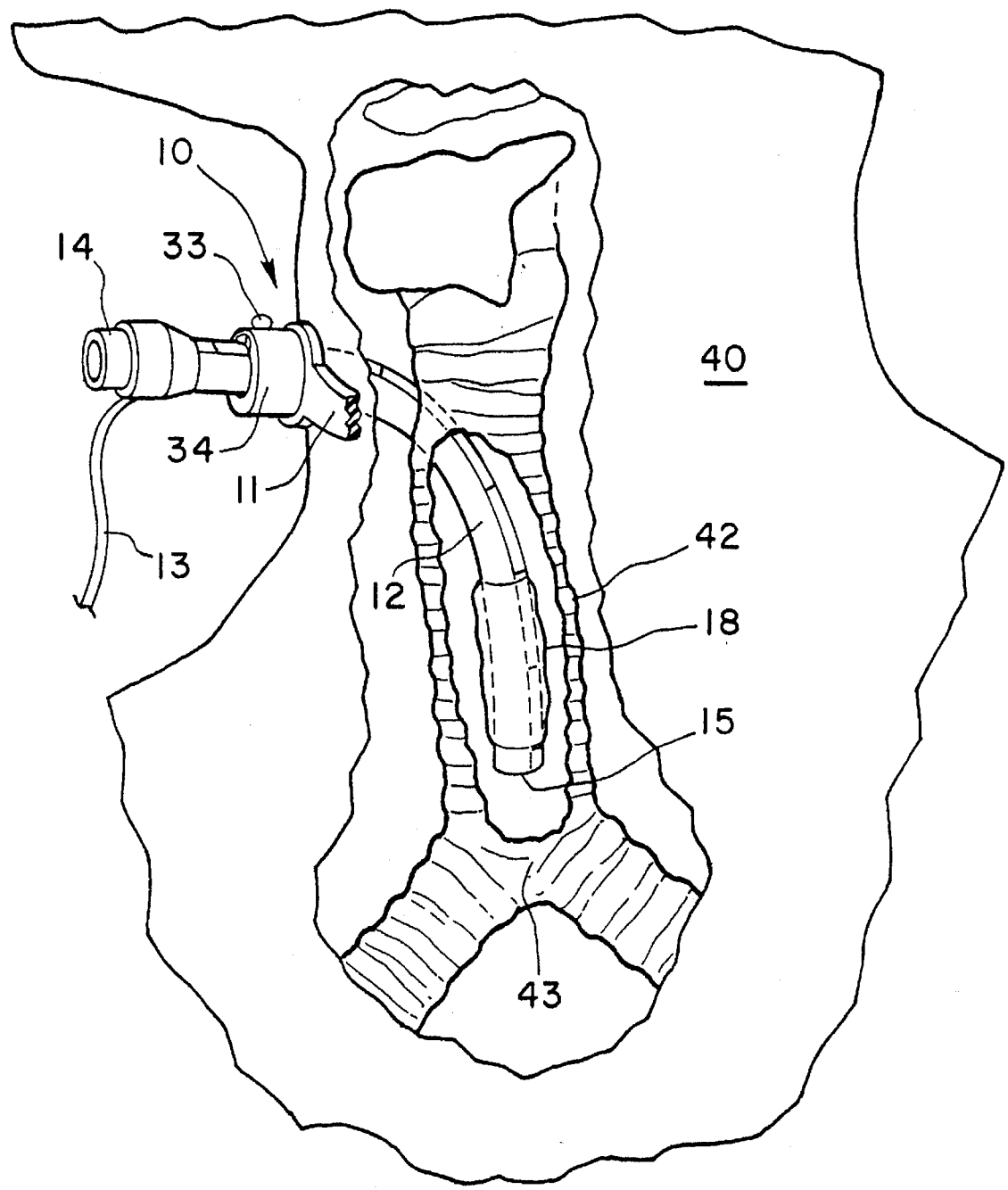
FIG. 11 is a cross-sectional view of the flexible tracheostomy tube corresponding to FIG. 9, after the ventilator has been disconnected from the patient and the cuff of the tracheostomy tube has been deflated.

FIGS. 10–12 illustrate the method used to wean a ventilator-dependent patient in the second embodiment of the present invention. The process begins as shown in FIG. 10 with the patient connected to an external ventilator through the flexible tracheostomy tube 10. The distal end 12 of the tracheostomy tube 10 has previously been inserted through an incision into the patient's trachea 42. The cuff 18 around the distal end 12 of the tracheostomy tube 10 is inflated to seal the region between the tracheostomy tube 10 and the patient's trachea 42.

To begin the weaning process, the ventilator cap 30 is disconnected from the proximal opening 14 of the tracheostomy tube 10 and the cuff 18 is deflated so that the patient can breathe spontaneously through the upper airway, as illustrated in FIG. 11. The health care provider adjusts the position of the neck flange 11 on the tracheostomy tube 10 and adjusts the position of the tracheostomy tube relative to the patient's trachea 42 so that the distal opening 15 of the tracheostomy tube 10 is located immediately above the patient's carina 43. For example, the physician can monitor the location of the distal end 15 of the tracheostomy tube 10 relative to the carina 43 by observing the radio-opaque markings on x-ray images of the patient's airway. Alternatively, the physician can directly observe the location of the tracheostomy tube through a conventional endoscope.

A transtracheal catheter 20 is then inserting through the tracheostomy tube 10 until the cap 26 is secured to the proximal opening 14 of the tracheostomy tube 10, as shown in FIG. 12. This should place the distal end 23 of the transtracheal catheter 20 approximately 1 to 2 cm above the distal opening 15 of the tracheostomy tube 10. A continuous flow of an oxygen/air mixture is then supplied through the transtracheal catheter and into the lungs of the patient. The flow of oxygen/air is initially supplied through the transtracheal catheter at a flow rate of about 8 to 20 liters per minute, and preferably about 10 liters per minute. A supply pressure of approximately 2 to 25 psi is satisfactory. The flow is gradually reduced over time to a minimal flow rate as the patient becomes accustomed to breathing without assistance of the ventilator. The concentration of oxygen in the gas mixture is gradually increased over time to meet the patient's oxygen need and compensate for the decreasing flow rate. This also helps to acclimate the patient to the higher oxygen concentrations commonly used in transtracheal oxygen therapy following the weaning process.

If necessary, the patient can be reconnected to the ventilator after a period of time. This is accomplished by removing the transtracheal catheter 20 from the tracheostomy tube 10, reinflating the cuff 18, and reconnecting the ventilator to the tracheostomy tube 10. The patient is allowed to remain on the ventilator for a period of time depending on the patient's condition and response to the weaning process. This sequence of steps is iteratively repeated while progressively increasing the length of time that the patient is disconnected from ventilator support during each iteration. In addition, the length of time that the patient is connected to the ventilator can be shortened during each iteration.

The transtracheal catheter 20 can also be temporarily removed from the tracheostomy tube 10 to allow the patient's secretions to be removed by suction, if necessary. For example, ventilator patients may experience respiratory difficulty due to accumulation of mucus in the lungs. The present invention provides a convenient means for suctioning out this mucus until the patient is strong enough to naturally clear the mucus from the lungs.

The above disclosure sets forth a number of embodiments of the present invention. Other arrangements or embodiments, not precisely set forth, could be practiced under the teachings of the present invention and as set forth in the following claims.

I claim:

1. A method for weaning a ventilator-dependent patient comprising:

ventilating the patient with a flexible tracheostomy tube having a proximal opening connected to a ventilator, a distal opening inserted through an incision into the patient's trachea, an inflatable cuff about said tracheostomy tube adjacent said distal opening for sealing the region between said tracheostomy tube and the patient's trachea, and an adjustable neck flange that can be adjustably positioned at a desired location along said tracheostomy tube for controlling the length of said tracheostomy tube extending into the patient's trachea;

disconnecting said ventilator from said proximal opening of said tracheostomy tube;

deflating said cuff so that the patient can breathe spontaneously through the patient's upper airway;

adjusting the position of said neck flange on said tracheostomy tube and adjusting the position of said tracheostomy tube relative to the patient's trachea so that said distal opening of said tracheostomy tube is located immediately above the patient's carina;

removably inserting a transtracheal catheter through said tracheostomy tube; and supplying a continuous flow of an oxygen/air mixture through said transtracheal catheter and into the lungs of the patient.

2. The method of claim 1 wherein said flow of oxygen/air is initially supplied through said transtracheal catheter at a flow rate of approximately 8 to 20 liters per minute.

3. The method of claim 1 wherein said flow of oxygen/air is initially supplied through said transtracheal catheter at a flow rate of approximately 10 liters per minute.

4. The method of claim 1 wherein said flow of oxygen/air through said transtracheal catheter is gradually reduced over time to a minimal flow rate.

5. The method of claim 4 wherein the concentration of oxygen in said flow of oxygen/air through said transtracheal catheter is gradually increased over time.

6. The method of claim 1 further comprising the additional steps of:

(a) reconnecting the patient to said ventilator after a first period of time by removing said transtracheal catheter from said tracheostomy tube, reinflating said cuff, and reconnecting said ventilator to said proximal opening of said tracheostomy tube;

(b) disconnecting the patient from said ventilator in accordance with the steps of claim 1 after a second period of time; and (c) iteratively repeating steps (a) and (b) with said first period of time progressively increasing.

7. The method of claim 1, wherein said oxygen/air mixture is supplied to said transtracheal catheter at a pressure of approximately 2 to 25 psi.

8. An apparatus for weaning a ventilator-dependent patient comprising:

a tracheostomy tube assembly having:

(a) a flexible tracheostomy tube with a proximal opening for connection to a ventilator and a distal portion with an opening for insertion through an incision into a patient's trachea;

(b) an adjustable neck flange that can be adjustably positioned at a desired location along said tracheostomy tube to adjustably control the length of said distal portion of said tracheostomy tube; and (c) an inflatable cuff extending around a portion of said distal portion of said tracheostomy tube for sealing the region between said distal portion of said tracheostomy tube and a patient's trachea while a patient is connected to said ventilator; and a transtracheal catheter having:

(a) a distal portion for removable insertion through said proximal opening of said tracheostomy tube after said ventilator has been disconnected, said distal portion having a length less than the length of said tracheostomy tube so that said distal portion remains within said tracheostomy tube;

(b) means for removably securing said transtracheal catheter to said proximal opening of said tracheostomy tube; and (c) a cap extending outward from said transtracheal catheter for at least partially blocking said proximal opening of said tracheostomy tube when said distal portion of said transtracheal catheter is inserted into said tracheostomy tube.

9. The apparatus of claim 8 wherein said tracheostomy tube assembly further comprises a helical reinforcing wire within said tracheostomy tube.

10. The apparatus of claim 8 wherein said neck flange can be adjusted to position said distal opening of said tracheostomy tube immediately above a patient's carina.

11. The apparatus of claim 8 wherein said transtracheal catheter has an outside diameter of approximately 3.5 millimeters or less.

12. The apparatus of claim 8 wherein said tracheostomy tube has an inside diameter of approximately 5 millimeters.

13. An apparatus for weaning ventilator-dependent patients comprising:

a tracheostomy tube assembly having:

(a) flexible tracheostomy tube with a proximal opening for connection to a ventilator and a distal portion with an opening for insertion through an incision into a patient's trachea;

(b) an adjustable neck flange that can be adjustably positioned at a desired location along said tracheostomy tube and thereby control the length of said distal portion of said tracheostomy tube;

(c) an inflatable cuff extending around said distal portion of said tracheostomy tube for sealing the region between said distal portion of said tracheostomy tube and a patient's trachea while a patient is connected to said ventilator; and (d) means for selectively inflating and deflating said cuff; and a transtracheal catheter having:

(a) a distal portion for removable insertion through said proximal opening of said tracheostomy tube, said distal portion having a length less than the length of said tracheostomy tube so that said distal portion remains within said tracheostomy tube;

(b) means for removably securing said transtracheal catheter to said proximal opening of said tracheostomy tube; and (c) a cap extending outward from said transtracheal catheter for at least partially blocking said proximal opening of said tracheostomy tube when said distal portion of said transtracheal catheter is inserted into said tracheostomy tube.

14. The apparatus of claim 13 wherein said tracheostomy tube assembly further comprises a helical reinforcing wire within said tracheostomy tube.

15. The apparatus of claim 13 wherein said neck flange can be adjusted to position said distal opening of said tracheostomy tube immediately above a patient's carina.

16. The apparatus of claim 13 wherein said transtracheal catheter has an inside diameter in the range of approximately 1.7 to 3 millimeters.

17. The apparatus of claim 13 wherein said transtracheal catheter has an outside diameter of approximately 3.5 millimeters or less.

18. The apparatus of claim 13 wherein said tracheostomy tube has an inside diameter of approximately 5 millimeters.

19. The apparatus of claim 13 wherein said transtracheal catheter has a length of approximately 20 to 22 centimeters.

* * * * *